(12) United States Patent
Takeuchi et al.

(10) Patent No.: US 10,551,355 B2
(45) Date of Patent: Feb. 4, 2020

(54) PROBE AND SUBJECT INFORMATION OBTAINING APPARATUS USING THE SAME

(71) Applicant: CANON KABUSHIKI KAISHA, Tokyo (JP)

(72) Inventors: Eiji Takeuchi, Kawasaki (JP); Yoshio Hotta, Kamakura (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 149 days.

(21) Appl. No.: 15/558,647

(22) PCT Filed: Mar. 22, 2016

(86) PCT No.: PCT/JP2016/001642
§ 371 (c)(1),
(2) Date: Sep. 15, 2017

(87) PCT Pub. No.: WO2016/157828
PCT Pub. Date: Oct. 6, 2016

(65) Prior Publication Data
US 2018/0106767 A1    Apr. 19, 2018

(30) Foreign Application Priority Data
Mar. 31, 2015   (JP) .................. 2015-074512

(51) Int. Cl.
*B06B 1/02* (2006.01)
*G10K 11/02* (2006.01)
*G01N 29/24* (2006.01)

(52) U.S. Cl.
CPC ....... *G01N 29/2406* (2013.01); *B06B 1/0292* (2013.01); *G01N 29/2418* (2013.01); *G10K 11/02* (2013.01); *B06B 2201/76* (2013.01)

(58) Field of Classification Search
CPC .............. B06B 1/0292; B06B 2201/76; G01N 29/2418; G01N 29/2406; G10K 11/02
(Continued)

(56) References Cited

U.S. PATENT DOCUMENTS

2010/0313667 A1* 12/2010 Terada .................... B32B 27/18
73/754
2011/0033699 A1*  2/2011 Hayashi .................... B32B 7/12
428/352

(Continued)

FOREIGN PATENT DOCUMENTS

EP   2130495   12/2009
EP   2511702   10/2012
(Continued)

*Primary Examiner* — Jacques M Saint Surin
(74) *Attorney, Agent, or Firm* — Venable LLP (57) ABSTRACT

Provided are a highly reliable probe including a light reflecting layer, which is resistant to the falling off of the light reflecting layer, and an information obtaining apparatus using the same. The probe includes: an element including at least one cell, each cell including a first electrode provided on a substrate, and a vibration membrane including a second electrode provided across a gap from the first electrode; an acoustic impedance matching layer disposed above the element; and a light reflecting layer. The light reflecting layer is fixed to the substrate via an adhesive layer.

18 Claims, 3 Drawing Sheets

(58) Field of Classification Search
USPC .......................................................... 73/643
See application file for complete search history.

(56) References Cited

U.S. PATENT DOCUMENTS

| | | | |
|---|---|---|---|
| 2011/0121291 A1* | 5/2011 | Chen | H01L 33/46 |
| | | | 257/43 |
| 2013/0255388 A1 | 10/2013 | Takeuchi et al. | G01N 29/2418 |
| 2013/0263669 A1* | 10/2013 | Nakanishi | G01H 9/00 |
| | | | 73/655 |
| 2014/0318254 A1 | 10/2014 | Torashima et al. | B06B 1/0292 |
| 2014/0318255 A1 | 10/2014 | Torashima et al. | B06B 1/0292 |
| 2015/0297091 A1* | 10/2015 | Nakatsuka | A61B 5/742 |
| | | | 600/407 |
| 2019/0046042 A1* | 2/2019 | Tokita | A61B 5/0095 |

FOREIGN PATENT DOCUMENTS

| | | |
|---|---|---|
| EP | 2719327 | 4/2014 |
| JP | 2008-125542 | 6/2008 |
| JP | 2012-222785 | 11/2012 |
| WO | WO 2008/114582 A1 | 9/2008 |

\* cited by examiner

PROBE AND SUBJECT INFORMATION OBTAINING APPARATUS USING THE SAME

TECHNICAL FIELD

The present invention relates to a probe, which includes a capacitive transducer or the like, and is configured to be used as, for example, a photoacoustic probe in an ultrasound diagnostic apparatus, and to a subject information obtaining apparatus using the probe.

BACKGROUND ART

There is given an ultrasound diagnostic apparatus configured to utilize photoacoustic waves. Photoacoustic waves are ultrasound waves that are generated when, for example, a pulse laser beam (electromagnetic waves) irradiating a body from the outside is absorbed by tissue inside the body. Photoacoustic waves are generated in a particular type of tissue in a body, and information of photoacoustic waves can therefore be utilized in the imaging of body tissue. Sound waves, ultrasound waves, photoacoustic waves, and the like that are called acoustic waves are herein represented by ultrasound waves in some places.

An ultrasound probe can be used to detect ultrasound waves generated inside a body. An ultrasound transducer is disposed inside an ultrasound probe to convert ultrasound waves into electric signals. While ultrasound transducers that utilize the piezoelectric effect have been hitherto in use, capacitive transducers are being actively researched and developed in recent years. In an example of capacitive transducers, two electrodes provided so as to sandwich a space that is called a cavity and that is kept in a substantially vacuum state form a cell, at least one cell forms an element, and at least one element is included in the capacitive transducer. One of the two electrodes is fixed to a membrane, and the thus built vibration membrane is held in a manner that allows the membrane to vibrate. Vibrations of the vibration membrane from ultrasound waves change the distance between the two electrodes, and the change in distance changes the capacitance. When a voltage is applied between the two electrodes in advance, the change in capacitance can be taken out as a current signal. This is an example of the principle of ultrasound reception operation. Capacitive transducers that are manufactured by applying a semiconductor micromachining technology are called capacitive micromachined ultrasonic transducers (CMUTs). An ultrasound probe having a plurality of densely packed elements is suitable for image quality enhancement. Such ultrasound probe is demanded of ultrasound diagnostic apparatus.

In the technical field described above, an acoustic impedance matching layer, which matches acoustic impedances (makes the acoustic impedance values close to one another) of all or some substances between the subject and the element, is provided above the element in some cases. A light reflecting layer is sometimes provided above the element to reduce noise that originates from light.

CITATION LIST

Patent Literature

PTL 1: Japanese Patent Application Laid-Open No. 2012-222785
PTL 2: International Publication WO2008/114582

SUMMARY OF INVENTION

Technical Problem

In an ultrasound probe, the acoustic impedance matching layer can be disposed above the element and the light reflecting layer can be disposed above the acoustic impedance matching layer. This configuration transmits ultrasound waves well while presenting difficulties for light to penetrate, and is therefore favorable. The acoustic impedance matching layer and the light reflecting layer can also function as a protective layer that protects the element from cuts and electric discharge. The acoustic impedance matching layer is formed thin in some ultrasound probes in order to reduce the attenuation of ultrasound waves within the acoustic impedance matching layer.

However, the acoustic impedance matching layer that is thin means less adhesive material and accordingly less adhesion for the acoustic impedance matching layer, which may result in the light reflecting layer falling off. When the light reflecting layer falls off, ultrasound transmittance and light transmittance are liable to change. The function as the protective layer for the element is also liable to suffer from the falling off. It is an object of the present invention to provide a highly reliable probe that has a light reflecting layer and an apparatus using the probe in order to solve these problems.

Solution to Problem

A probe according to one embodiment of the present invention includes: an element including at least one cell, each of the at least one cell including a first electrode provided on a substrate, and a vibration membrane including a second electrode provided across a gap from the first electrode; an acoustic impedance matching layer disposed above the element; and a light reflecting layer. In the probe, the light reflecting layer is fixed to the substrate via an adhesive layer.

A probe according to another embodiment of the present invention includes: an element including at least one cell, each of the at least one cell including a first electrode provided on a substrate, and a vibration membrane including a second electrode provided above the first electrode with a gap interposed between the first electrode and the second electrode; and an acoustic impedance matching layer disposed above the element. Further, the acoustic impedance matching layer is covered with a light reflecting layer, the light reflecting layer being provided on a surface of the acoustic impedance matching layer that is opposite from a surface where the element is formed, and a first adhesive layer is provided to fix the light reflecting layer to the substrate.

Advantageous Effects of Invention

Having the adhesive layer, the probe according to the one embodiment of the present invention does not allow the light reflecting layer to fall off easily and is accordingly high in reliability.

Further features of the present invention will become apparent from the following description of exemplary embodiments with reference to the attached drawings.

DESCRIPTION OF EMBODIMENTS

Preferred embodiments of the present invention will now be described in detail in accordance with the accompanying drawings.

In a probe of the present invention, an acoustic impedance matching layer and a light reflecting layer are formed above a capacitive transducer, which is provided on a substrate, and the light reflecting layer is fixed to the substrate via a first adhesive layer. Embodiments of the present invention based on this concept are described below. However, the present invention is not limited to those embodiments, and various modifications and changes can be made without departing from the spirit of the present invention.

First Embodiment

Figure 1A:
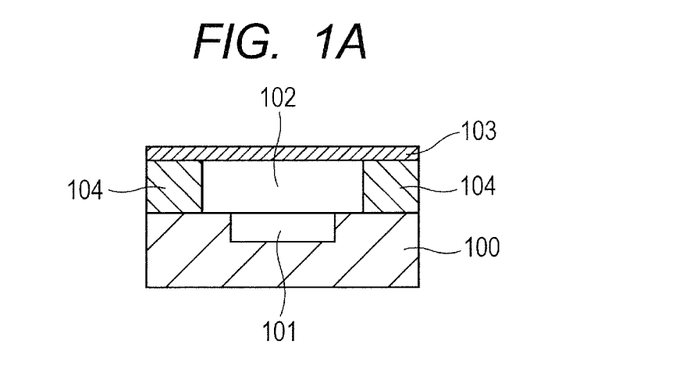
FIG. 1A is a sectional view for illustrating an embodiment of the present invention.
Figure 1B:
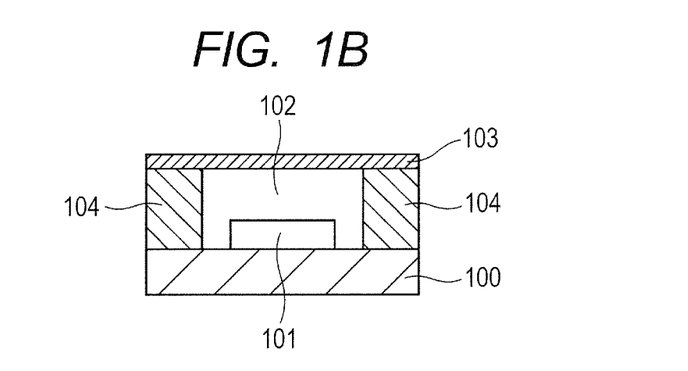
FIG. 1B is a sectional view for illustrating an embodiment of the present invention.

A first embodiment of the present invention is described below with reference to the drawings. FIG. 1A and FIG. 1B are sectional views for illustrating the first embodiment of the present invention. An element 101, which has at least one cell, is disposed in a substrate 100. An acoustic impedance matching layer 102 is disposed right above the element 101. A light reflecting layer 103 faces and covers the acoustic impedance matching layer 102. The light reflecting layer 103 is fixed to the substrate 100 via an adhesive layer 104. A principal surface of the light reflecting layer 103 (a surface parallel to or substantially parallel to a surface of the substrate 100) is made broader than a principal surface of the acoustic impedance matching layer 102. With this, the light reflecting layer 103 can be fixed to the substrate 100 without the intervening acoustic impedance matching layer 102. In this configuration, all or some of the acoustic impedance matching layer 102, the light reflecting layer 103, and the adhesive layer 104 have the role of a protective layer that protects the element 101.

The element 101 illustrated in FIG. 1A is embedded in the substrate 100. The element 101 may mounted on the substrate 100 as illustrated in FIG. 1B. In short, while a difference in manufacturing method or the like may make a difference in whether the element 101 is embedded in the substrate or mounted on the top of the substrate 100, this is not an important point in the present invention and the present invention is applicable to any structure. In FIG. 1A and FIG. 1B, the adhesive layer 104 is positioned so as to surround the perimeter of the element 101.

The shape of the acoustic impedance matching layer 102 viewed from above is not limited and can be circular or quadrangular, for example. However, it is preferred to dispose the acoustic impedance matching layer 102 so as to cover the entire element 101 in order not to hinder the propagation of ultrasound waves. For high reliability, it is preferred to avoid giving the acoustic impedance matching layer 102 too large an area, while a large area is preferred for the adhesive layer 104. These areas, however, are not limited in the present invention. The adhesive layer 104 is disposed so as to surround the perimeter of the acoustic impedance matching layer 102.

A material that is favorable for the acoustic impedance matching layer 102 when acoustic impedance, adhesion, and the like are taken into consideration is a silicone-resin based adhesive, for example. The acoustic impedance matching function can be adjusted by, for example, a method that involves introducing a fluorine base or the like into silicone oil itself. There is also a method of changing acoustic impedance in which the density of an adhesive is increased by adding fine powder to the adhesive at a high density. A specific example of the material of the acoustic impedance matching layer 102 is X-32-1619 (a product of Shin-Etsu Chemical Co., Ltd.).

The light reflecting layer 103 that is preferred is high in light reflectance and high in sound transmittance. For example, the light reflecting layer 103 can be fabricated by forming a metal thin film by vapor deposition on a thin resin film. However, the light reflecting layer 103 is not limited thereto. The metal thin film, which can be formed from Au or other high reflectance materials, is also not limited to this material.

The adhesive layer 104 that is preferred has strong adhesion. Having strong adhesion is preferred also when the adhesive layer 104 is formed thin in order to make the acoustic impedance matching layer 102 thin. In the case where a silicone resin is used for the acoustic impedance matching layer 102, a material of the same base is preferred for the adhesive layer 104 in order not to inhibit curing. To give a more specific example, in the case where a silicone resin in which a fluorine base is introduced for acoustic impedance matching is employed and an addition curing system (a type in which a resin is cured in a short time by heat through the action of a platinum catalyst) is introduced, favorable adhesion is achieved by employing an adhesive of the same silicone resin addition type for the adhesive layer 104. A specific example of the adhesive layer material is X-32-949 (a product of Shin-Etsu Chemical Co., Ltd.), but any addition reaction-type material can be employed and the adhesive layer 104 is not limited thereto. For example, room temperature vulcanizing (RTV) rubber, which is an adhesion grade, can be employed to increase the adhesion of the adhesive layer 104.

Effects of forming the acoustic impedance matching layer 102 thin are described next. The acoustic impedance matching layer 102 is sometimes formed thin in order to, for example, reduce the attenuation of ultrasound. The thickness of the acoustic impedance matching layer 102 also affects the path length of a reflected ultrasound wave at an upper interface and lower interface of the acoustic impedance matching layer 102. Changing the thickness of the acoustic impedance matching layer 102 accordingly changes the waveform of an ultrasound wave that enters the element 101. The addition of the reflected wave may generate an image that should not be present (an artifact) in a processed image, and a change in the waveform of an incident ultrasound wave changes the way artifacts are generated. The acoustic impedance matching layer 102 is sometimes formed thin for this reason.

Figure 6A:
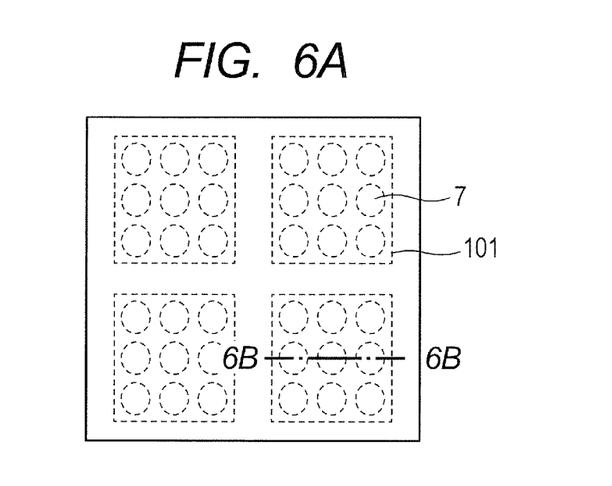
FIG. 6A is a view for illustrating an example of a capacitive transducer.
Figure 6B:
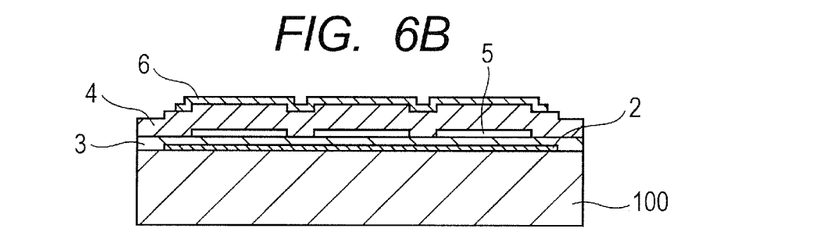
FIG. 6B is a view for illustrating an example of a capacitive transducer.

An example of the capacitive transducer is described next. FIG. 6A and FIG. 6B are views for illustrating an example of the capacitive transducer in which each element 101 includes a plurality of cells 7. FIG. 6A is a top view and FIG. 6B is a sectional view taken along the line 6B-6B of FIG. 6A. This transducer has a plurality of elements 101, each of which includes the cells 7. The shape of each element 101 which is quadrangular in FIG. 6A and FIG. 6B is not limited and may be circular, for example. While each of the four elements 101 has nine cells 7 in FIG. 6A and FIG. 6B, the cell count in each element 101 can be any number that is equal to or more than 1.

Each cell 7 in this example includes, as illustrated in FIG. 6B, a substrate 100 (which can be the same substrate as the substrate 100 in FIG. 1A and FIG. 1B), a first electrode 2, an insulating film 3 on the first electrode 2, a vibration membrane 4 supported to the insulating film 3 via a gap 5 (an empty gap or the like) in a manner that allows the vibration membrane 4 to vibrate, and a second electrode 6 on the vibration membrane 4. The substrate 100, which is made from Si, may instead be an insulating substrate made of glass or the like. The first electrode 2 is formed from a thin film of metal such as titanium or aluminum. In the case where the substrate 100 is formed from silicon that is low in resistance, the substrate 100 may be used as the first electrode 2. The insulating film 3 can be formed from a thin film of silicon oxide or the like by deposition. The vibration membrane 4 and a vibration membrane supporting portion, which supports the vibration membrane 4, are formed from a thin film of silicon nitride or the like by deposition. The second electrode 6 can be made from a thin film of metal such as titanium or aluminum. A membrane portion of the vibration membrane film that is made from a silicon nitride film or a single-crystal silicon film, in combination with the second electrode portion, may be viewed as a vibration membrane. Each element in this example thus includes at least one cell in which a vibration membrane that includes one of two electrodes provided so as to sandwich a gap is supported in a manner that allows the vibration membrane to vibrate.

In the example of FIG. 6A and FIG. 6B, an acoustic impedance matching layer covers the entire element 101, a light reflecting layer covers the acoustic impedance matching layer, and an edge portion of the light reflecting layer is adhered to the substrate 100 by an adhesive layer. The adhesive layer is adhered to the substrate 100 outside the element 101.

A driving principle of the transducer of this example is described. The cells are formed from the first electrode 2 and the vibration membrane, which are provided across the gap 5 from each other. A direct current voltage is therefore applied to the first electrode 2 or the second electrode 6 in order to receive an acoustic wave. This bias voltage is applied by a voltage applying unit. A received acoustic wave vibrates the vibration membrane, thereby changing the distance across (the height of) the gap and accordingly changing the capacitance between the electrodes. The change in capacitance is detected at the first electrode 2 or the second electrode 6, and the acoustic wave is thus detected. A reception signal generated from the change in capacitance is sent to an amplifier circuit. The element 101 is also capable of transmitting an acoustic wave by applying an alternating current voltage to the first electrode 2 or the second electrode 6 and vibrating the vibration membrane in this manner. A transmission signal generated from this application of an alternating current voltage is transmitted from a transmission/reception circuit to the element 101.

According to the first embodiment of the present invention described above, a highly reliable probe that is resistant to the falling off of a light reflecting layer can be provided.

An example of a manufacturing method of the present invention is described next. The light reflecting layer 103 is formed by forming a gold film (a reflective film) on one side of a resin film through vapor deposition. A silicone resin-based adhesive is applied by screen printing to a surface of the light reflecting layer 103 that is opposite from the surface on which the gold film has been formed by vapor deposition. The applied adhesive is thermally cured to form the acoustic impedance matching layer 102. Meanwhile, the element 101 is formed by a semiconductor process on the substrate 100, and a silicone resin-based adhesive is applied to the substrate 100. The acoustic impedance matching layer 102 formed on the light reflecting layer 103 is disposed right above the element 101 so as to face the element 101.

Next, a flat board is used to apply pressure to the surface of the light reflecting layer 103 on which the gold film has been formed, thereby bringing the silicone resin-based adhesive into close contact with the surface opposite from the surface where the gold film has been formed by vapor deposition. This silicone resin-based adhesive is thermally cured to form the adhesive layer 104. The light reflecting layer 103 and the adhesive layer 104 are both soft prior to curing, and the thickness of the adhesive layer 104 can be made equal to the thickness of the acoustic impedance matching layer 102 by the pressurization with the use of the flat board.

The manufacturing method of the present invention is not limited to the one described above. For instance, the acoustic impedance matching layer 102 may be formed on the element 101 instead of on the light reflecting layer 103. Specifically, the acoustic impedance matching layer is formed on one of the substrate, and the surface of the light reflecting layer 103 that is opposite from the surface of the light reflecting layer on which the reflective film has been formed, and the material of a first adhesive layer is applied to the other of the substrate and the opposite surface. The light reflecting layer and the substrate are then laid on top of each other, with the acoustic impedance matching layer disposed right above the element. Pressure is then applied to the surface of the light reflecting layer on which the reflective film has been formed to bring the material of the first adhesive layer into close contact and thus form the first adhesive layer. The acoustic impedance matching layer 102 can have a uniform thickness when formed by screen printing. However, the method of forming the acoustic impedance matching layer 102 is not limited to screen printing. Offset printing can be employed as well in the case where the acoustic impedance matching layer 102 is to be formed to a thickness less than 10 µm. In the case where the acoustic impedance matching layer 102 is to be formed to a thickness of 10 µm or more, screen printing, stencil mask printing, or squeegee printing that uses a mask member can be employed. Another way to form the adhesive layer 104 includes applying an adhesive to one or both of the substrate 100 and the light reflecting layer 103, subsequently sticking the substrate 100 and the light reflecting layer 103 together, and curing the adhesive. A highly reliable ultrasound probe that is resistant to the falling off of a light reflecting layer is provided through the manufacturing method described above.

Figure 2:
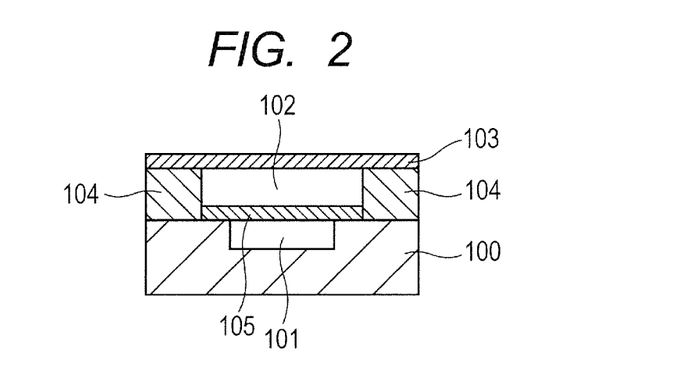
FIG. 2 is a sectional view for illustrating another embodiment of the present invention.

The following configuration may also be employed. FIG. 2 is a sectional view for illustrating another embodiment of the present invention in which a second adhesive layer 105 is formed between the element 101 and the acoustic impedance matching layer 102. This configuration prevents the element 101 and the acoustic impedance matching layer 102 from separating from each other.

Figure 3:
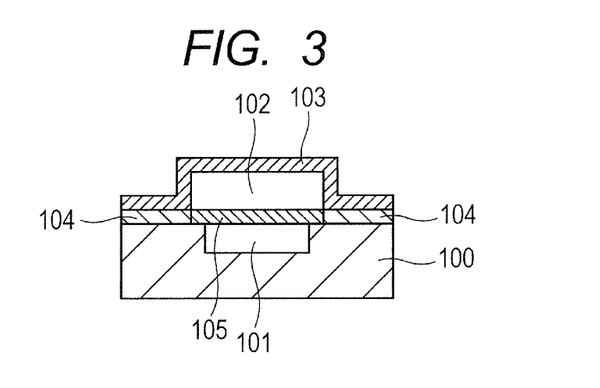
FIG. 3 is a sectional view for illustrating another embodiment of the present invention.
Figure 5:
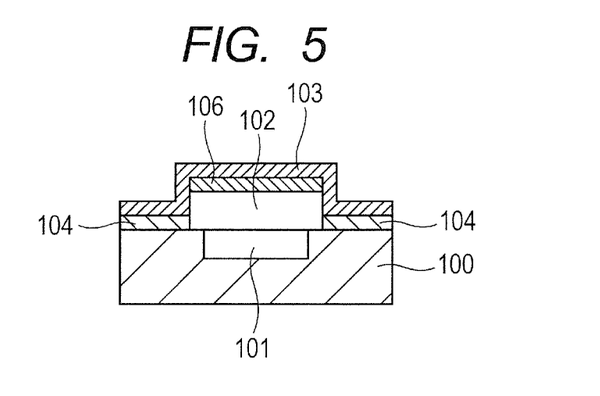
FIG. 5 is a sectional view for illustrating another embodiment of the present invention.

A configuration of FIG. 3 may also be employed in which the acoustic impedance matching layer 102 and the adhesive layer 104 have different thicknesses. This configuration allows the thickness of the acoustic impedance matching layer 102 to be flexible in order to determine what waveform an ultrasound wave that enters the element 101 is to have. The configuration also allows the thickness of the adhesive layer 104 to be flexible in order to enhance the adhesion between the substrate and the light reflecting layer. The second adhesive layer 105 provided between the element 101 and the acoustic impedance matching layer 102 in the configuration of FIG. 3 may be omitted as in FIG. 5.

Figure 4:
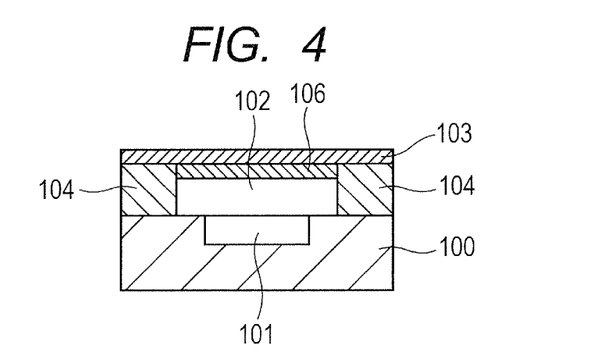
FIG. 4 is a sectional view for illustrating another embodiment of the present invention.

A configuration of FIG. 4 may also be employed in which a third adhesive layer 106 is formed between the acoustic impedance matching layer 102 and the light reflecting layer 103. This configuration prevents the light reflecting layer 103 and the acoustic impedance matching layer 102 from separating from each other. The structure of FIG. 2 and the structure of FIG. 4 may be combined so that the adhesive layers 105 and 106 are provided above and below the acoustic impedance matching layer 102 each. A configuration of FIG. 4 may also be modified so that the acoustic impedance matching layer 102 and the adhesive layer 104 have different thicknesses as in FIG. 5. With this configuration, the thickness of the acoustic impedance matching layer 102 can be determined based on what waveform an ultrasound wave that enters the element 101 is to have. Another advantage of this configuration is that the adhesive layer 104 can be set to a thickness that enhances the adhesion between the substrate 100 and the light reflecting layer 103. In the configuration of FIG. 2 to the configuration of FIG. 5, the adhesive layers 104, 105 and 106 are greater in adhesion than the acoustic impedance matching layer 102. In other words, the adhesive layers 104, 105 and 106 are clearly distinguishable from the acoustic impedance matching layer 102, and the main function of the adhesive layers 104, 105 and 106 is to bond layers together, whereas the acoustic impedance matching layer 102 mainly handles impedance matching.

In the case where the second adhesive layer 105 or the third adhesive layer 106 is formed in addition to the first adhesive layer 104 as described above, forming the second or third adhesive layer at the same time as the first adhesive layer is formed simplifies the manufacture. An example of this manufacturing method is described below through the embodiment illustrated in the sectional view of FIG. 2. The light reflecting layer 103 is formed by forming a gold film on one side of a resin film through vapor deposition. A silicone resin-based adhesive is formed as the acoustic impedance matching layer 102 by screen printing on a surface of the light reflecting layer 103 that is opposite from the surface on which the gold film has been formed by vapor deposition. Meanwhile, a silicone resin-based adhesive for forming the second adhesive layer 105 is applied right above the element 101, which is formed on the substrate 100. A silicone resin-based adhesive for forming the first adhesive layer 104 is applied to other regions of the top surface of the substrate 100 than the region right above the element 101. The acoustic impedance matching layer 102 formed on the light reflecting layer 103 is then disposed right above the element 101 so as to face the element 101. Next, a flat board is used to apply pressure to the surface of the light reflecting layer 103 on which the gold film has been formed, thereby bringing the silicone resin-based adhesives into close contact. The silicone resin-based adhesives are thermally cured to form the first adhesive layer 104 and the second adhesive layer 105. The first adhesive layer 104 and the second adhesive layer 105 may be formed from the same material or different materials. When the same material is used for the first adhesive layer 104 and the second adhesive layer 105, the adhesive needs to be applied only once, which makes the manufacturing method even more simpler.

In the case of the embodiment of FIG. 4, on the surface of the light reflecting layer 103 that is opposite from the surface on which the gold film has been formed by vapor deposition, the material of the third adhesive layer 106 is applied to a region that later occupies the space right above the element 101, and the material of the first adhesive layer 104 is applied to other regions than the one that later occupies the space right above the element 101. Meanwhile, the acoustic impedance matching layer 102 is formed on the substrate 100 right above the element 101. Pressure is next applied with the use of a flat board to the surface of the light reflecting layer 103 on which the gold film has been formed as in the manufacturing method described above, thereby bringing the material of the first adhesive layer into close contact with other regions of the substrate than the region right above the element, and bringing the material of the third adhesive layer into close contact with the acoustic impedance matching layer. The first adhesive layer 104 and the third adhesive layer 106 are formed in the same step in this manner.

Example 1

More specific Example 1 of the present invention is described below. In Example 1, the element 101 was fabricated by a semiconductor process on a silicon wafer having a thickness of 300 µm. The element 101 viewed from above was shaped like a circle having a diameter of 2 mm. The substrate 100 having a length of 6 mm and a width of 5 mm was cut by dicing out of the silicon wafer where the element was formed.

Meanwhile, a Au film having a thickness of 10 nm was formed by vapor deposition on one side of a PET film having a thickness of 12 µm. On a surface of the light reflecting layer 103 opposite from the Au film, X-32-1619 (a product of Shin-Etsu Chemical Co., Ltd.), which is a silicone resin-based adhesive, was printed by screen printing to a thickness of 30 µm in the shape of a circle having a diameter of 3 mm. The silicone resin-based adhesive was cured by heating at 80° C. for an hour, thus forming the acoustic impedance matching layer 102.

Next, X-32-949 (a product of Shin-Etsu Chemical Co., Ltd.) was applied as a silicone resin-based adhesive for forming the first adhesive layer 104 to the substrate 100 where the element 101 had been formed. The acoustic impedance matching layer 102 formed on the light reflecting layer 103 was disposed right above the element 101 so as to face the element 101. A flat board was used next to apply pressure to the surface of the light reflecting layer 103 on which the gold film had been formed, thereby bringing the silicone resin-based adhesive into close contact with the substrate 100. The silicone resin-based adhesive was cured by heating at 80° C. for an hour, and the adhesive layer 104 was thus formed.

A tensile test was conducted on the light reflecting layer of the thus manufactured probe to check the peel strength. The test showed that the light reflecting layer had a peel strength approximately twice greater than that of a sample having no adhesive layer 104. It was thus confirmed that the light reflecting layer was resistant to peeling and high in reliability.

Another Embodiment

The probe described above is applicable to subject information obtaining apparatus such as ultrasound diagnostic apparatus. The transducer receives an acoustic wave from a subject and outputs electric signals, which are used to obtain subject information that reflects the subject's optical characteristics value such as light absorption coefficient, or subject information that reflects a difference in acoustic impedance.

More specifically, an example of the information obtaining apparatus irradiates a subject with light (electromagnetic waves including visible rays and infrared rays). Photoacoustic waves generated as a result at a plurality of points (sites) inside the subject are received to obtain a characteristics distribution indicating the distribution of pieces of characteristics information that correspond to the plurality of points inside the subject. The characteristics information obtained from photoacoustic waves is characteristics information related to the absorption of light, and includes characteristics information that reflects the initial sound pressure of photoacoustic waves generated by the light irradiation, or a light energy absorption density derived from the initial sound pressure, or that reflects the absorption coefficient, the concentration of a substance that forms tissue, or the like. The substance concentration is, for example, the oxygen saturation level, the total hemoglobin concentration, the concentration of oxyhemoglobin or deoxyhemoglobin, or the like. The information obtaining apparatus may be purposed for making a diagnosis of a malignant tumor or a vascular disease in humans or animals, a follow-up observation of chemical treatment, or the like. Intended subjects of diagnosis are therefore living bodies, specifically, the breasts, neck, abdomen, or the like of a human or an animal. A light absorber inside a subject that absorbs the light of the apparatus is tissue having an absorption coefficient that is relatively high compared to others within the subject. For example, when the subject is a human body part, light absorbers are oxyhemoglobin and deoxyhemoglobin, blood vessels where oxyhemoglobin and deoxyhemoglobin are contained in a large amount, tumors that include new blood vessels, plaques in the carotid wall, and the like. Molecular probes that utilize gold particles, graphite, or the like to couple differentially to a malignant tumor or the like, and capsules delivering medicine are also light absorbers.

The distribution of data related to acoustic characteristics inside a subject may be obtained by receiving other waves than photoacoustic waves, and the received waves may be reflected waves that are generated by an ultrasound echo that is a reflection, inside the subject, of ultrasound waves transmitted from a probe that includes a transducer. This distribution of data related to acoustic characteristics includes a distribution that reflects a difference in acoustic impedance between different types of tissue inside the subject.

Figure 7:
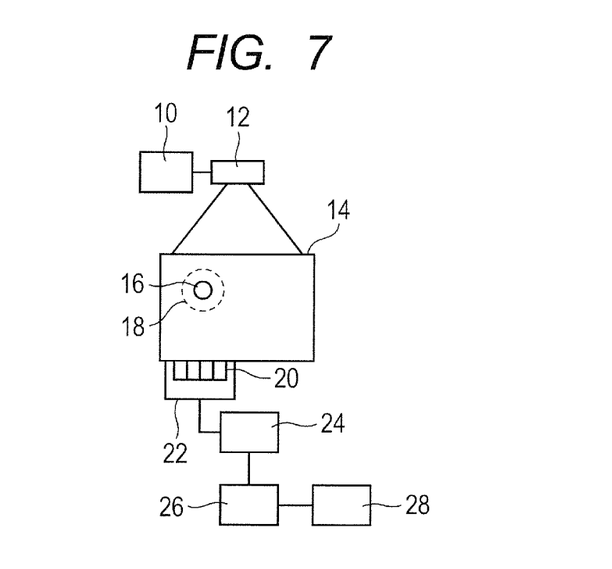
FIG. 7 is an overall block diagram for illustrating an example of an information obtaining apparatus that includes a probe of the present invention.

FIG. 7 is a diagram for illustrating the information obtaining apparatus that utilizes photoacoustic effects. Pulse light emitted by a light source 10 irradiates a subject 14 via an optical member 12, which includes a lens, a mirror, an optical fiber, and the like. A light absorber 16 inside the subject 14 absorbs the energy of the pulse light, and generates a photoacoustic wave 18, which is an acoustic wave. A probe 20 of the present invention inside a probe unit 22 receives the photoacoustic wave 18, converts the received wave into electric signals, and outputs the electric signals to a front end circuit of the probe unit 22. The front end circuit executes signal processing such as pre-amplification, and outputs the processed signals to a signal processing unit 24 of a main body unit via a connection unit. The signal processing unit 24 performs signal processing such as A/D conversion and amplification on the input electric signals, and outputs the processed signals to a data processing unit 26, which is included in the main body unit as well. The data processing unit 26 uses the input signals to obtain subject information (characteristics information that reflects the subject's optical characteristics value such as a light absorption coefficient) as image data. Here, the signal processing unit 24 and the data processing unit 26 are together referred to as processing unit. A display unit 28 displays an image based on the image data input from the data processing unit 26. The probe unit 22 and the main body unit may be configured unitarily.

INDUSTRIAL APPLICABILITY

The probe of the present invention can be used in ultrasound diagnostic apparatus and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-074512, filed Mar. 31, 2015, which is hereby incorporated by reference herein in its entirety.

REFERENCE SIGNS LIST

100 . . . substrate, 101 . . . element, 102 . . . acoustic impedance matching layer, 103 . . . light reflecting layer, 104 . . . first adhesive layer, 105 . . . second adhesive layer, 106 . . . third adhesive layer

The invention claimed is:
1. A probe comprising:
an element comprising at least one cell, each cell comprising a first electrode provided on a substrate, and a vibration membrane comprising a second electrode provided across a gap from the first electrode;
an acoustic impedance matching layer disposed above the element;
a light reflecting layer; and
an adhesive layer adhering the light reflecting layer to the substrate and adhering the acoustic impedance matching layer to the substrate.
2. A probe according to claim 1, wherein the adhesive layer has adhesion greater than adhesion of the acoustic impedance matching layer.
3. A probe according to claim 1, further comprising a second adhesive layer between the element and the acoustic impedance matching layer.
4. A probe according to claim 1, further comprising a third adhesive layer between the light reflecting layer and the acoustic impedance matching layer.
5. A probe according to claim 1, wherein the adhesive layer is disposed so as to surround a perimeter of the element.

6. A probe comprising:
an element comprising at least one cell, each cell comprising a first electrode provided on a substrate, and a vibration membrane comprising a second electrode provided above the first electrode with a gap interposed between the first electrode and the second electrode; and
an acoustic impedance matching layer disposed above the element,
wherein the acoustic impedance matching layer is covered with a light reflecting layer, the light reflecting layer being provided on a surface of the acoustic impedance matching layer that is opposite from a surface where the element is formed, and a first adhesive layer is provided to adhere the light reflecting layer to the substrate and to adhere the acoustic impedance matching layer to the substrate.

7. A probe according to claim 6, further comprising a second adhesive layer between the element and the acoustic impedance matching layer.

8. A probe according to claim 6, further comprising a third adhesive layer between the light reflecting layer and the acoustic impedance matching layer.

9. A probe according to claim 6, wherein the first adhesive layer and the acoustic impedance matching layer have the same thickness.

10. A probe according to claim 1, wherein the first adhesive layer and the acoustic impedance matching layer have different thicknesses.

11. A probe according to claim 6, wherein the acoustic impedance matching layer comprises a silicone resin-based adhesive.

12. A probe according to claim 11, wherein the adhesive layer comprises a silicone resin-based adhesive.

13. A probe according to claim 6, wherein the light reflecting layer comprises a layer created by forming a thin metal film on a resin film.

14. A method of manufacturing the probe of claim 7, wherein the first adhesive layer and the second adhesive layer are formed in the same step.

15. A method of manufacturing the probe according to claim 14 comprising:

forming the acoustic impedance matching layer on a surface of the light reflecting layer that is opposite from a surface where a reflective film is formed;
applying a material of the second adhesive layer right above the element formed on the substrate, and applying a material of the first adhesive layer to other regions of the substrate than a region right above the element;
disposing the acoustic impedance matching layer formed on the light reflecting layer right above the element so as to face the element; and
applying pressure to the surface of the light reflecting layer on which the reflective film is formed, to thereby bring the material of the first adhesive layer into close contact with the opposite surface of the light reflecting layer and to bring the material of the second adhesive layer into close contact with the acoustic impedance matching layer, and thus forming the first adhesive layer and the second adhesive layer.

16. A method of manufacturing the probe of claim 1, wherein the acoustic impedance matching layer is formed by one of screen printing, offset printing, stencil mask printing, and squeegee printing, that uses a mask member.

17. A subject information obtaining apparatus, comprising:
a light source;
a probe configured to receive an acoustic wave that is generated by irradiating a subject with light emitted from the light source to convert the received acoustic wave into electric signals; and
a processing unit configured to obtain information of the subject by using the electric signals,
wherein the probe comprises the probe of claim 1.

18. A subject information obtaining apparatus comprising:
a light source;
a probe configured to receive an acoustic wave that is generated by irradiating a subject with light emitted from the light source to convert the received acoustic wave into electric signals; and
a processing unit configured to obtain information of the subject by using the electric signals,
wherein the probe comprises the probe of claim 6.

* * * * *